US006387236B2

(12) United States Patent
Nordman et al.

(10) Patent No.: US 6,387,236 B2
(45) Date of Patent: May 14, 2002

(54) MULTI-CHANNEL CAPILLARY ELECTROPHORESIS DEVICE INCLUDING SHEATH-FLOW CUVETTE AND REPLACEABLE CAPILLARY ARRAY

(75) Inventors: Eric S. Nordman, Palo Alto; John Shigeura, Fremont; Albert L. Carrillo, Redwood City; David M. Demorest, Soquel; Philip J. Wunderle, El Sobrante, all of CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/805,624

(22) Filed: Mar. 13, 2001

Related U.S. Application Data

(60) Continuation of application No. 09/621,071, filed on Jul. 21, 2000, now Pat. No. 6,231,739, which is a division of application No. 09/151,928, filed on Sep. 11, 1998, now Pat. No. 6,162,341.

(51) Int. Cl.[7] .................. G01N 27/26; G01N 27/447

(52) U.S. Cl. .................. 204/601; 204/451; 204/452; 204/453; 204/603; 204/604; 422/99; 422/100; 422/104

(58) Field of Search .................. 422/99, 100, 104; 204/451, 452, 453, 454, 455, 601, 602, 603, 604, 605

(56) References Cited

U.S. PATENT DOCUMENTS

| | | | |
|---|---|---|---|
| 4,811,218 A | 3/1989 | Hunkapiller et al. | 204/461 |
| 5,274,240 A | 12/1993 | Mathies et al. | 250/458.1 |
| 5,277,780 A | 1/1994 | Kambara | |
| 5,439,578 A | 8/1995 | Dovichi et al. | 204/603 |
| 5,516,409 A | 5/1996 | Kambara | 204/603 |
| 5,667,656 A | 9/1997 | Kambara | 204/603 |
| 6,054,032 A | 4/2000 | Haddad et al. | 204/451 |
| 6,162,341 A | * 12/2000 | Nordman et al. | 204/603 |
| 6,231,739 B1 | * 5/2001 | Nordman et al. | 204/601 |

FOREIGN PATENT DOCUMENTS

| | | |
|---|---|---|
| EP | 0723149 | 7/1996 |
| WO | WO9938005 | 7/1999 |

OTHER PUBLICATIONS

Bashkin, J.S. et al., "Implementation of a Capillary Array Electrophoresis Instrument," *Journal of Capillary Electrophoresis*, 1996, vol. 3, Issue 2, pp. 61–68.

Marsh, M. et al., "High–throughput DNA Sequencing on a Capillary Array Electrophoresis System," *Journal of Capillary Electrophoresis*, 1997, vol. 4, Issue 3, pp. 83–89.

Cheng et al., *Science*, vol. 242, Oct. 28, 1988, pp. 562–564.

Cheng Y F et al., "Interaction of Capillary Zone electrophoresis with a Sheath Flow Cuvette Detector," *Analytical Chemistry*, US, American Chemical Society, Columbus, vol. 62, No. 5, Mar. 1, 1990, pp. 496–503.

K. Ueno et al., *Analytical Chemistry*, vol. 66, No. 9, May 1, 1994, pp. 1424–1431.

Woolley et al., "High–Speed DNA Genotyping Using Microfabricated Capillary Array Electrophoresis Chips," *Anal. Chem.* 69 (11) :2181–2186 (Jun. 1, 1997).

\* cited by examiner

*Primary Examiner*—Jill Warden
*Assistant Examiner*—John S. Starsiak, Jr.
(74) *Attorney, Agent, or Firm*—Kilyk & Bowersox, P.L.L.C.

(57) ABSTRACT

A multi-channel capillary electrophoresis apparatus is disclosed. The apparatus includes a capillary array assembly comprising a plurality of capillaries, each capillary having a capillary outlet, and an outlet support for supporting the capillary outlets. The apparatus further includes a cuvette defining a receiving slot, a gap region, and a detection zone, where the receiving slot is adapted to removably receive the outlet support, and wherein when the outlet support is inserted into the receiving slot, the capillary outlets are positioned in the gap region in proximity to the detection zone, and a flow channel is formed by the outlet support and the receiving slot such that the flow channel is in fluid communication with the gap region. In addition, the apparatus includes a front plumbing block in fluid communication with the flow channel for supplying a fluid flow through the gap region sufficient to transport material downstream from the capillary outlets to the detection zone.

1 Claim, 18 Drawing Sheets

MULTI-CHANNEL CAPILLARY ELECTROPHORESIS DEVICE INCLUDING SHEATH-FLOW CUVETTE AND REPLACEABLE CAPILLARY ARRAY

CROSS REFERENCE TO RELATED APPLICATIONS

This application is a continuation of application Ser. No. 09/621,071 filed Jul. 21, 2000, now U.S. Pat. No. 6,231,739 which is a divisional of application Ser. No. 09/151,928, filed Sep. 11, 1998, now U.S. Pat. No. 6,162,341, all of which are incorporated herein by reference.

FIELD OF THE INVENTION

This invention relates to apparatus and methods useful for biochemical analysis. More specifically, this invention relates to a highly automated capillary electrophoresis apparatus for the simultaneous analysis of multiple samples, and methods for using such apparatus.

BACKGROUND

Capillary electrophoresis (CE) is a powerful analytical separation technique that brings speed, quantitation, reproducibility and automation to the inherently highly resolving but typically labor intensive methods of electrophoresis (e.g., *Capillary Electrophoresis Theory and Practice*, Grossman and Colburn, eds., Academic Press (1992)). While early capillary electrophoresis systems utilized only a single capillary tube, multi-capillary systems have been developed to provide increased throughput (e.g., Mathies et al., U.S. Pat. No. 5,247,240; Dovichi and Zhang, U.S. Pat. No. 5,439,578; Kambara, U.S. Pat. No. 5,516,406; Takahashi, et al., *Anal. Chem.*, 66: 1021–1026 (1994)). Such multi-capillary CE systems are particularly attractive for use in large scale DNA sequencing projects.

However, existing multi-channel capillary electrophoresis systems have several significant shortcomings that limit their utility, particularly for applications requiring a high degree of automation, throughput, detection sensitivity and reliability. For example, existing systems do not provide for a sheath-flow detection cuvette wherein a capillary array may be replaced by a user without extensive disassembly of the cuvette. In addition, existing systems do not provide for a sheath-flow detection cuvette wherein fresh separation media and/or capillary wash solutions may be introduced into outlets of the capillary tubes under high pressure. Thus, there remains a continuing need for an automated multi-channel capillary electrophoresis device including these features.

SUMMARY

The present invention is directed towards our discovery of a multi-channel capillary electrophoresis device including a sheath-flow detection cuvette wherein a capillary array is easily replaceable by a user, and wherein fresh separation media and/or capillary wash solutions may be introduced into outlets of the capillary tubes under high pressure.

In a first aspect, the invention comprises a multi-channel capillary electrophoresis apparatus. The apparatus includes a capillary array assembly comprising a plurality of capillaries, each capillary having an outlet, and an outlet support for supporting the capillary outlets. In addition, the apparatus includes a cuvette defining a receiving slot, a gap region, and a detection zone, where the receiving slot of the cuvette is adapted to removably receive the outlet support. When the outlet support is inserted into the receiving slot, the capillary outlets are positioned in the gap region in proximity to the detection zone, and a flow channel is formed by the outlet support and the receiving slot such that the flow channel is in fluid communication with the gap region. The apparatus further includes a plumbing block in fluid communication with the flow channel for supplying a fluid flow through the gap region sufficient to transport material downstream from the capillary outlets to the detection zone.

These and other features and advantages of the present invention will become better understood with reference to the following description, drawings, and appended claims.

DETAILED DESCRIPTION OF THE PREFERRED EMBODIMENTS

Figure 1:
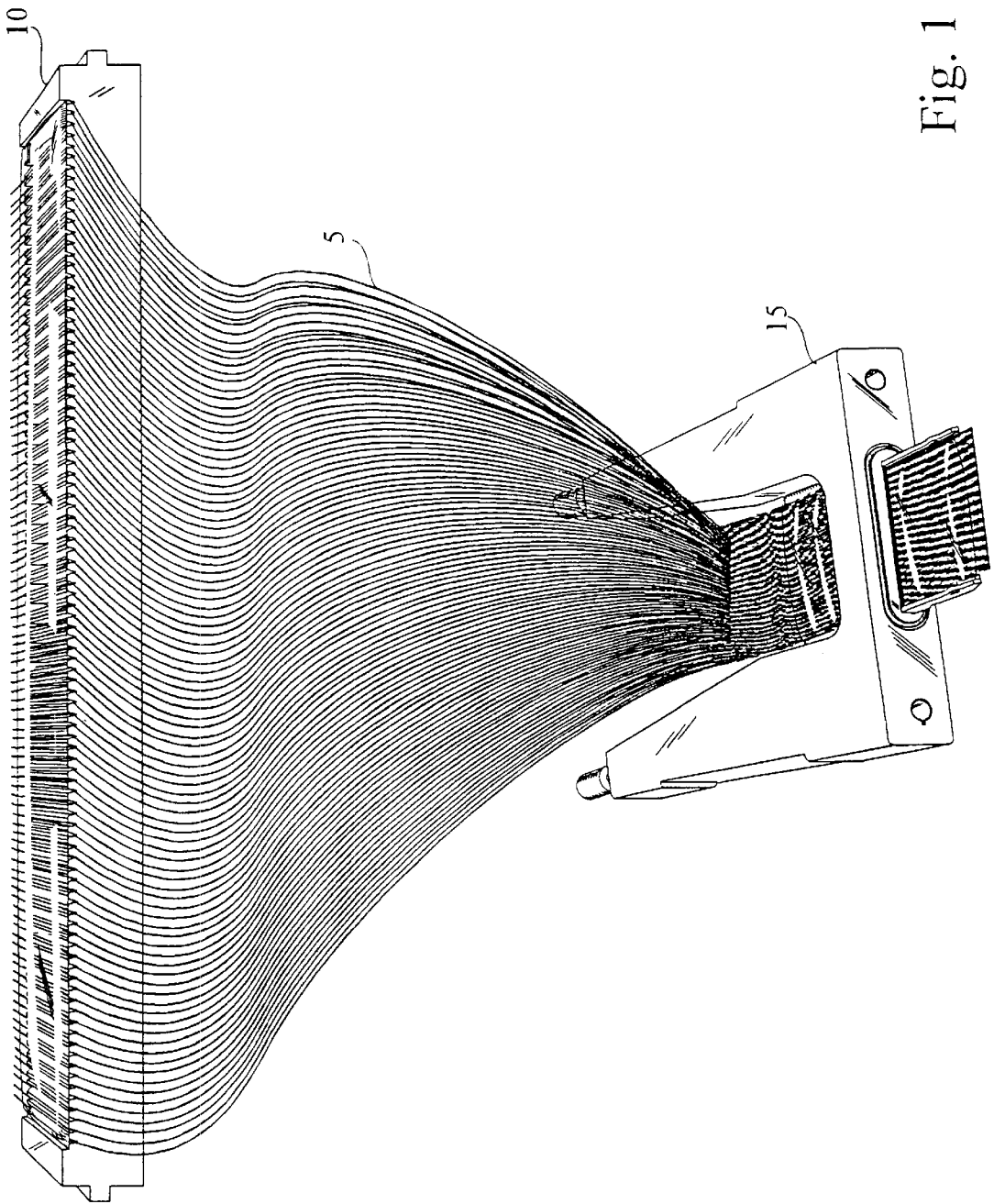
FIG. 1 shows a perspective view of a preferred capillary array assembly with an outlet support in the foreground.

Reference will now be made in detail to several preferred embodiments of the invention, examples of which are illustrated in the accompanying drawings. While the invention will be described in conjunction with these preferred embodiments, it will be understood that they are not intended to limit the invention to these embodiments. On the contrary, the invention is intended to cover alternatives, modifications, and equivalents, that may be included within the invention as defined by the appended claims.

Generally, the present invention is directed to a multi-channel capillary electrophoresis device comprising a capillary array assembly and a cuvette assembly for use in a sheath-flow detection system wherein the capillary array assembly is adapted to be removably inserted into the cuvette assembly such that the capillary array assembly may be easily replaced by a user. In addition, the cuvette is adapted to permit a high-pressure flow of fluid through the cuvette into outlets of the capillary tubes for filling the capillary tubes with fresh separation medium and/or wash solutions.

I. Definitions

Unless stated otherwise, the following terms and phrases as used herein are intended to have the following meanings:

"Sheath-flow detection system" means a detection system wherein a sample is detected outside of a separation capillary after being transported from an outlet of such capillary into a detection zone by a flow of a "sheath fluid" (e.g., Cheng and Dovichi, *Science* 242: 562–564 (1988); Kambara and Takahashi, *Nature* 361, :565–566 (1993)). The sheath fluid may be any fluid capable of supporting a sample eluting from the capillary outlet. Preferred sheath fluids include aqueous buffers, both with and without polymers dissolved therein. In a particularly preferred embodiment of the present invention, the sheath fluid is the separation medium used to effect the electrophoretic separation in the capillary tubes, e.g., a flowable solution containing an un-crosslinked polymer.

"Separation medium" refers to a medium located within the lumen of a capillary tube within which an electrophoretic separation is conducted. Exemplary separation media include crosslinked gels, un-crosslinked polymer solutions, or polymer-free solvents, e.g., buffered water. Optionally, separation media may include denaturants such as detergents, e.g., SDS, or organics, e.g., urea, formamide, or pyrrolidinone.

II. Capillary Array Assmbly

The capillary array assembly of the present invention provides a means for arranging an array of capillary electrophoresis tubes in an automated multi-channel capillary electrophoresis system. More particularly, the capillary array assembly (1) allows the capillary array to be easily removed from and introduced into the capillary electrophoresis system, e.g., to facilitate replacement of the capillary tubes, (2) provides an interface between the capillary tubes and a sheath-flow detection system, (3) facilitates alignment of the capillary outlets with an optical detection system, and (4) effects alignment of the capillary inlets with sample reservoirs.

Figure 2:
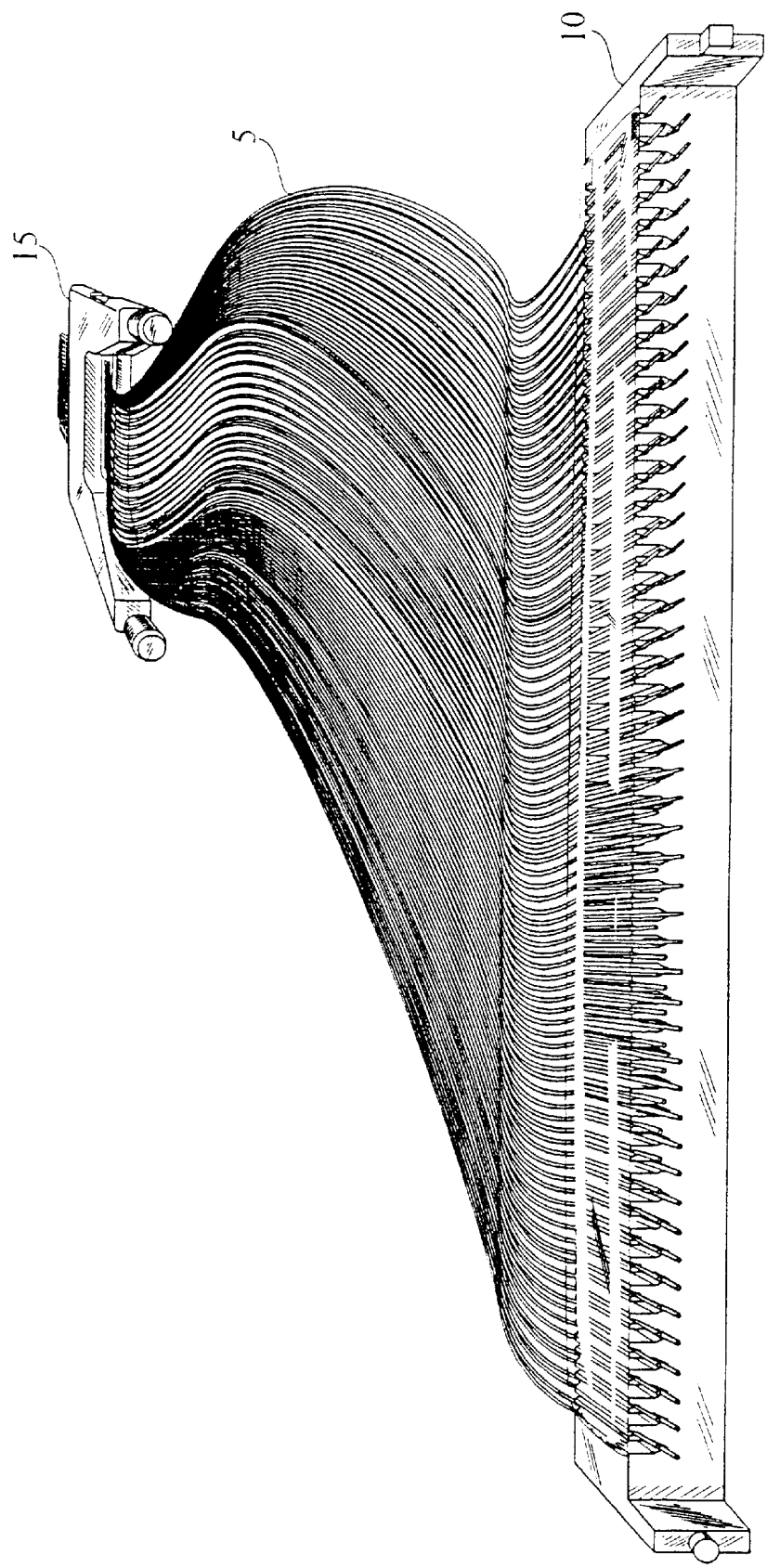
FIG. 2 shows a perspective view of a preferred capillary array assembly with an inlet support in the foreground.

Generally, the capillary array assembly of the present invention comprises (1) a plurality of capillary tubes, (2) an inlet support for supporting inlet ends of the capillaries in registration with a plurality of sample reservoirs, and (3) an outlet support for supporting outlet ends of the capillaries and for locating such outlet ends with respect to a sheath-flow detection system. FIGS. 1 and 2 show perspective views of a preferred embodiment of a capillary array assembly according to the present invention having 104 capillary tubes 5, an inlet support 10, and an outlet support 15.

1. Capillaries.

The capillaries of the present invention are tubes or channels or other structure capable of supporting a volume of separation medium suitable for carrying out an electrophoretic separation. The geometry of a capillary may vary widely and includes tubes with circular, rectangular or square cross-sections, channels, groves, plates, and the like, and may be fabricated by a wide range of well known technologies. An important feature of a capillary for use with the invention is the surface-to-volume ratio of the capillary lumen. High values of this ratio permit efficient dissipation of the Joule heat produced in the separation medium during electrophoresis. Preferably, ratios in the range of about 0.4 to 0.04 $\mu m^{-1}$ are employed. These ratio values correspond to the surface-to-volume ratios of tubular capillaries with circular cross-sections having inside diameters in the range of about 10 $\mu m$ to about 100 $\mu m$.

Preferably, capillaries for use with the invention are made of silica, fused silica, quartz, silicate-based glass, such as borosilicate glass, phosphate glass, alumina-containing glass, or other silica-like materials, or from plastics, e.g., polycarbonate or acrylic.

Where the capillaries are in the form of discrete capillary tubes, e.g., fused silica capillary tubes, preferably the outside surfaces of the capillaries are coated with a material to protect the capillaries from breakage, e.g., a polyimide, Teflon, acrylic or other polymeric coating (e.g., Polymicro Technologies, AZ). However, as will be discussed in more detail below, if the capillaries have a coating or cladding on their outside walls, and the properties of the coating are such that the coating interferes with the detection process, e.g., fluorescent detection is used and the coating material is fluorescent, the coating should be removed adjacent to the capillary outlets, e.g., by laser ablation.

Figure 3:
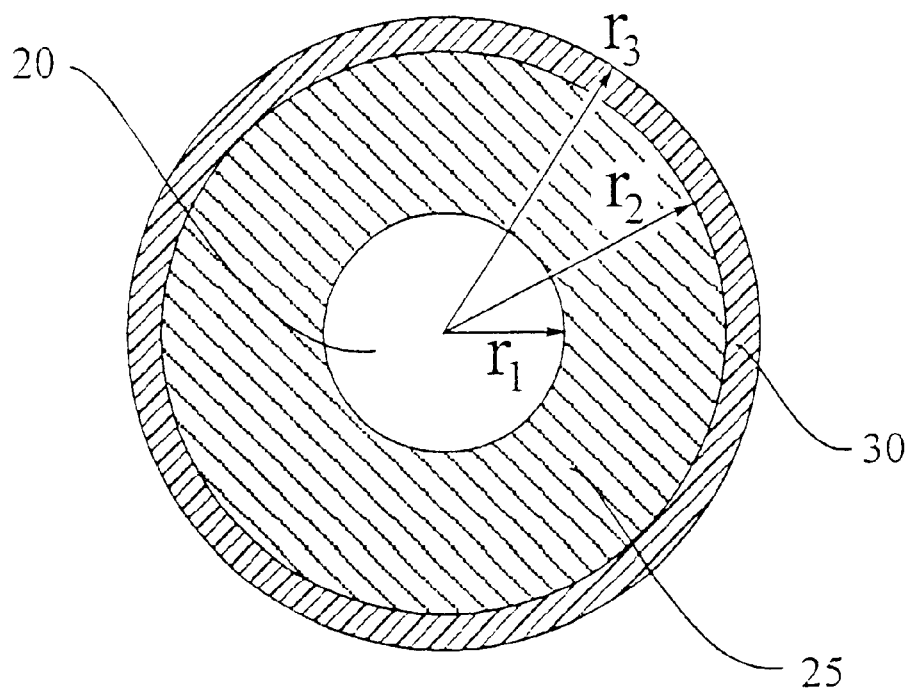
FIG. 3 shows a cross-section of a preferred capillary tube.

Referring to FIG. 3, the capillary tubes of a preferred embodiment of the invention are characterized by a lumen 20 having an inner radius $r_1$, a wall 25 having a thickness $r_2$-$r_1$, an outer coating 30 having a thickness $r_3$- $r_2$, and a length L. Preferably the inner radius is between about 5 $\mu m$ and 100 $\mu m$, the wall has a thickness of between about 20 $\mu m$ and about 150 $\mu m$, and the outer coating has a thickness of between about 2 $\mu m$ and 10 $\mu m$. Preferred outer coatings include polyimide, Teflon, acrylic, and the like. The preferred length of the capillary tubes used in the present invention will depend upon the speed and resolution of the separation required in a particular application. Generally, as the capillary length is increased, the resolution of the separation is increased while the speed of the separation is decreased. However, typically the capillaries will be between about 10 cm and 100 cm in length.

To increase the throughput of the capillary electrophoresis device of the present invention, a plurality of capillaries are used. Preferably between about 10 to 1000 capillaries, and more preferably between about 20 and 200 capillaries are used.

The capillaries may be multiple individual capillary tubes, as shown in FIGS. 1 and 2, or they may be formed in a monolithic substrate, e.g., in a micromachined device (e.g., Soane and Soane, U.S. Pat. No. 5,750,015; and Mathies et al., *Analytical Chemistry*, 69: 2181–2186 (1997)). Preferably, in the present invention, the capillary tubes are individual capillary tubes formed from fused silica having an outside surface coated with a polyimide coating.

2. Inlet Support.

The inlet support of the capillary array assembly of the present invention serves to position the capillary inlets in registration with sample reservoirs containing samples to be analyzed. Such registration is required to effect efficient and reproducible injection of samples into each capillary of the capillary array.

Figure 4:
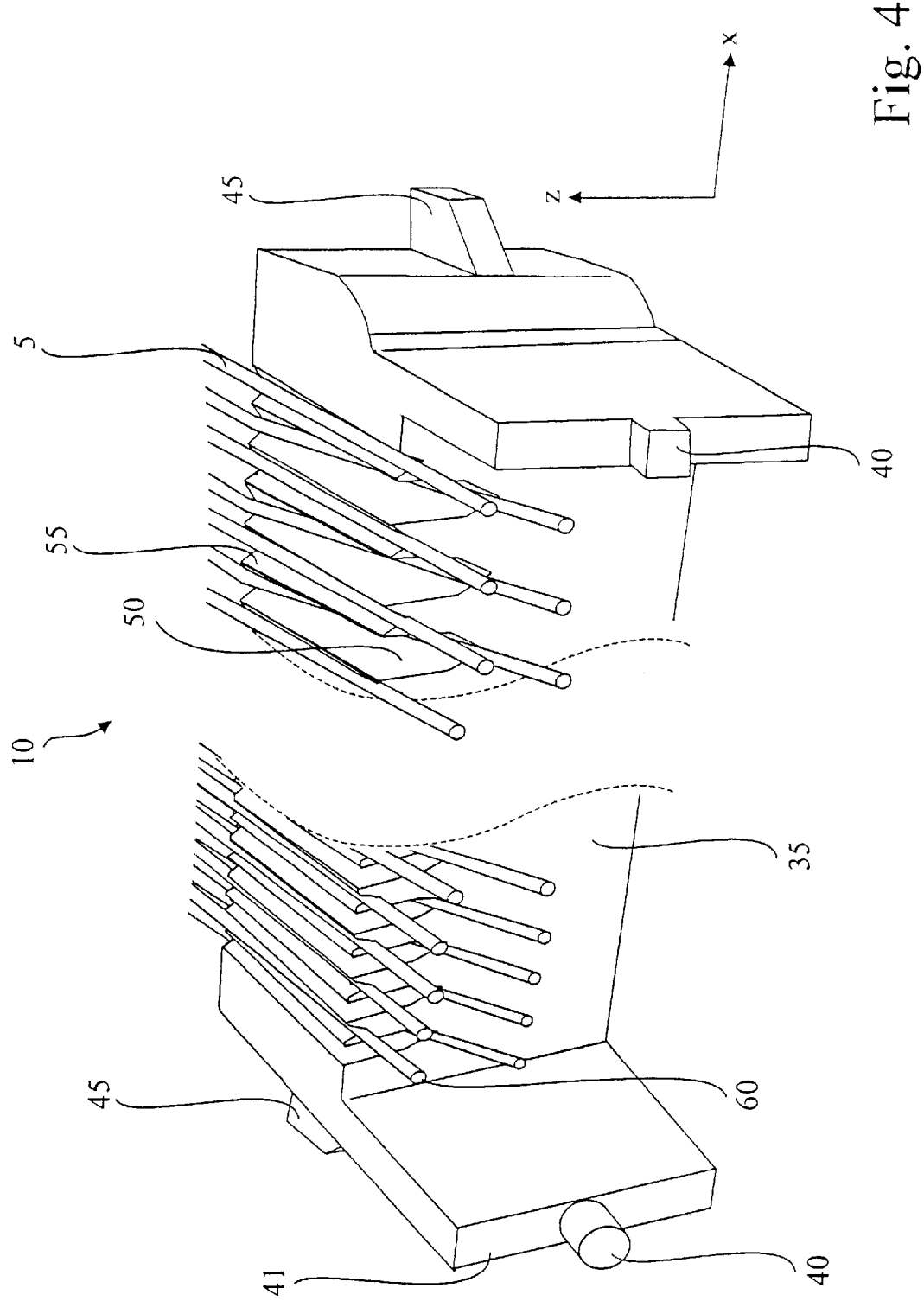
FIG. 4 shows a perspective view of a preferred inlet support.

FIG. 4 shows a perspective view of a preferred embodiment of an inlet support 10 of the present invention including capillary tubes 5 mounted therein. The inlet support of this preferred embodiment comprises a body 35, registration features 40 and 45, and upper 55 and lower 50 capillary alignment grooves.

Figure 5:
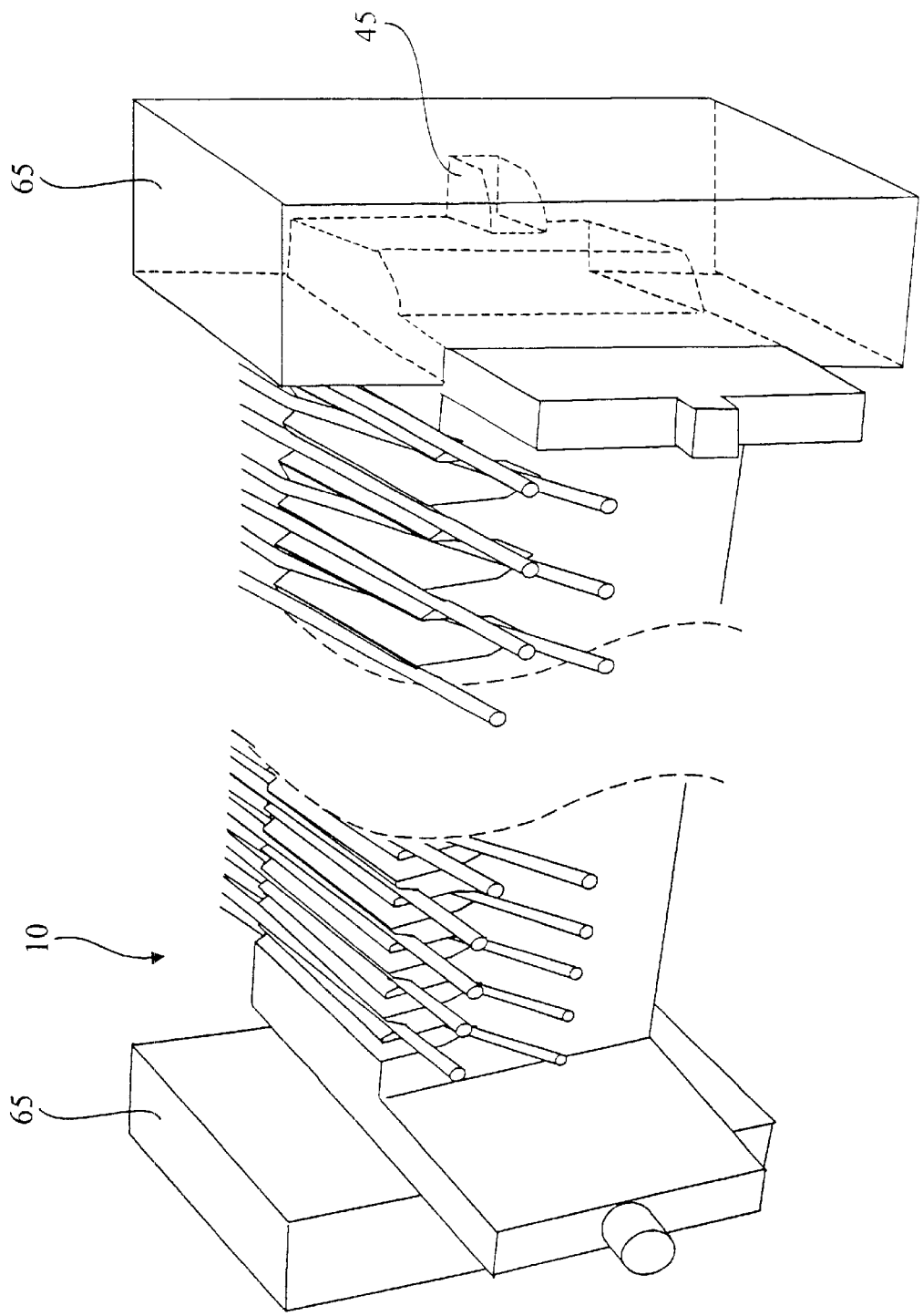
FIG. 5 shows a perspective view of a preferred inlet support wherein the inlet support is registered with respect to a frame member.

Registration features 40 and 45 serve to align the inlet support with respect to sample reservoirs containing samples to be analyzed. In particular, registration features 40 serve to align the inlet support with respect to a contact surface 41 associated with the sample reservoirs 70, and registration features 45 serve to guide the inlet support into a proper position with respect to the sample wells. Registration features 40 determine the length of the capillary tubes that enter into the sample wells. FIG. 5 shows the inlet support 10 fitted into frame members 65 with which the registration features 45 are engaged.

Alignment grooves 50 and 55 serve to hold inlets 60 of capillaries 5 in a defined and fixed position relative to the body 35 of the inlet support. Preferably, the alignment grooves have a V-shape to more accurately locate the capillary tubes therein. The pitch of the grooves may be any pitch that conforms to a pitch of the sample reservoirs to be addressed. However, it is preferred that the pitch of the grooves be an integral fraction of 9 mm in order to effect registration of a multi-channel pipette with both sample reservoirs arranged in a traditional 96-well microtiter plate configuration and the capillary inlets. Thus, exemplary preferred pitches are 9 mm, 9/2 mm, 9/3 mm, etc. The alignment grooves of the inlet support shown in FIG. 4 have a two-tier configuration comprising an upper tier of V-grooves 55 and a lower tier of V-grooves 50. This multi-tier configuration is advantageous because it allows for more wells to be located in a given linear dimension. This is important because the maximum spacing of the capillary inlets is constrained by the spacing of the capillary outlets, and the spacing of the capillary outlets is typically made as small as possible to facilitate sample detection. In addition, the multi-tier arrangement facilitates access to the sample wells by a sample delivery device, e.g., a robotically-controlled micro-pipette.

Preferably, to secure the capillary inlets into the alignment grooves 50 and 55, portions of the capillaries adjacent to the inlets are potted into the alignment grooves with a potting agent (not shown). Particularly preferred potting agents include epoxy and silicone adhesives.

Figure 6:
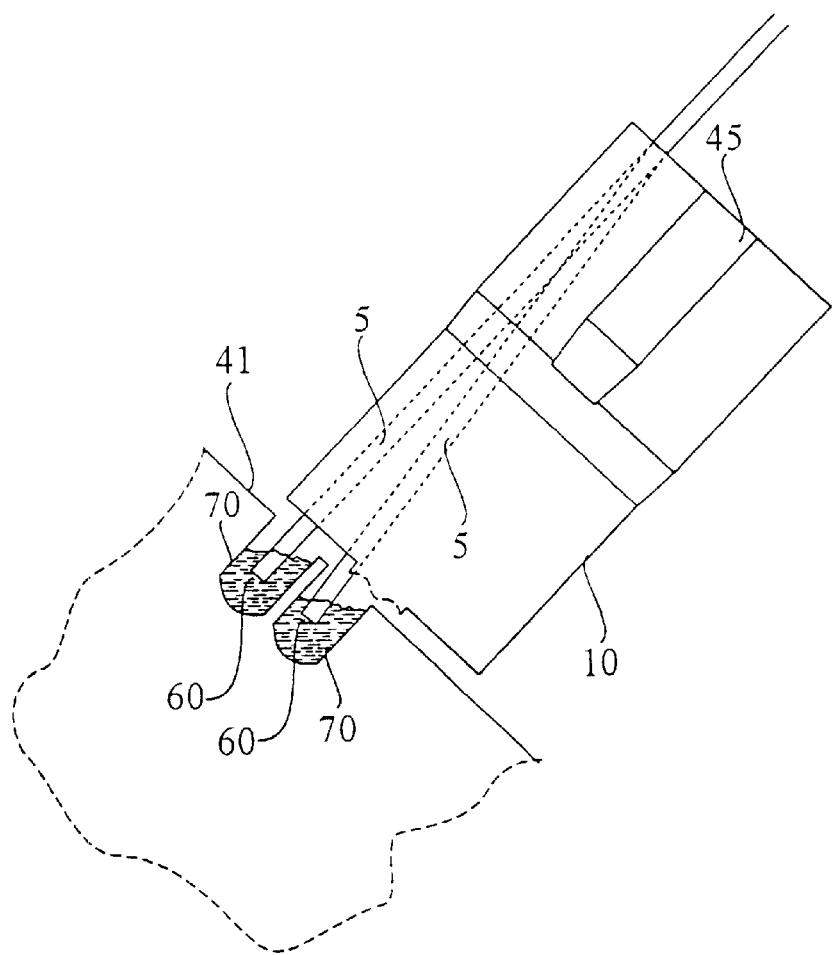
FIG. 6 shows a side view of a preferred inlet support.
Figure 7:
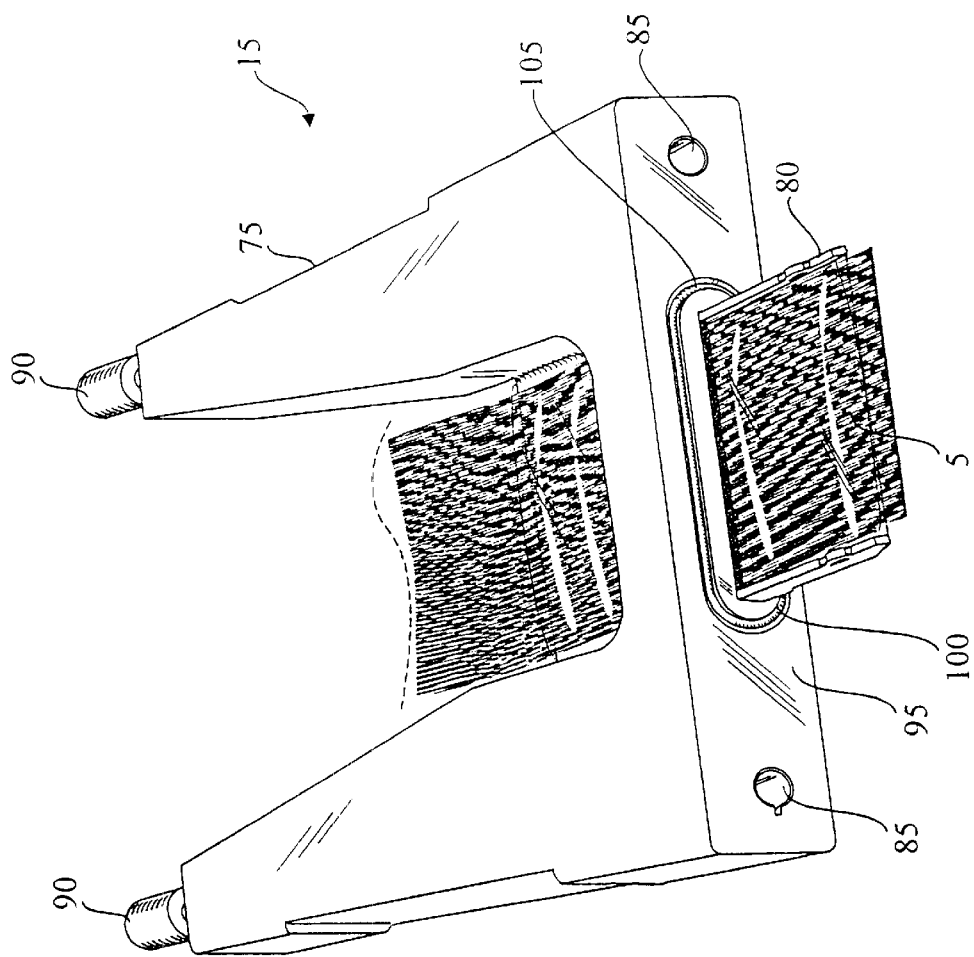
FIG. 7 shows a perspective view of a preferred outlet support.

As most clearly illustrated in FIG. 6, the capillary inlets are positioned in the inlet support such that the capillary inlets 60 are suspended away from the body of the inlet support in order to facilitate insertion of the inlets into sample reservoirs 70.

3. Outlet Support.

The outlet support of the present invention performs a number of important functions including (1) aligning the capillary outlets with respect to an optical detection system, (2) aligning the capillary outlets with respect to a sheath-flow fluid delivery system such that a sheath fluid carries sample material from the capillary outlets into a sheath-flow stream, (3) creating a pressure-tight seal between the capillary tubes of the capillary array and the sheath-flow flow delivery system, and (4) providing a mechanism whereby the capillaries may be easily replaced by a user.

A preferred outlet support 15 of the present invention is shown in FIGS. 7–10. The major components of this preferred outlet support include a base 75 and a platform 80. The base 75 includes guide-holes 85 into which guide-pins (not show) may be inserted in order to locate the outlet support with respect to a cuvette assembly. The base further includes fasteners 90 to securely attach the outlet support to the cuvette assembly and create a pressure-tight seal between the cuvette assembly and the outlet support. Preferably, these fasteners are stainless steel thumb screws. A front face 95 of the base further includes a sealing member 100 to form a pressure-tight seal between the outlet support and the cuvette assembly to which it mates such that the platform 80 is circumscribed by the sealing member. The sealing member is preferably an o-ring formed from an elastomeric polymer, e.g., ethylene-propylene rubber, or a fluoroelastomer, e.g., Viton. The o-ring is located in an o-ring registration groove 106 to precisely locate the o-ring with respect to the platform.

Figure 8:
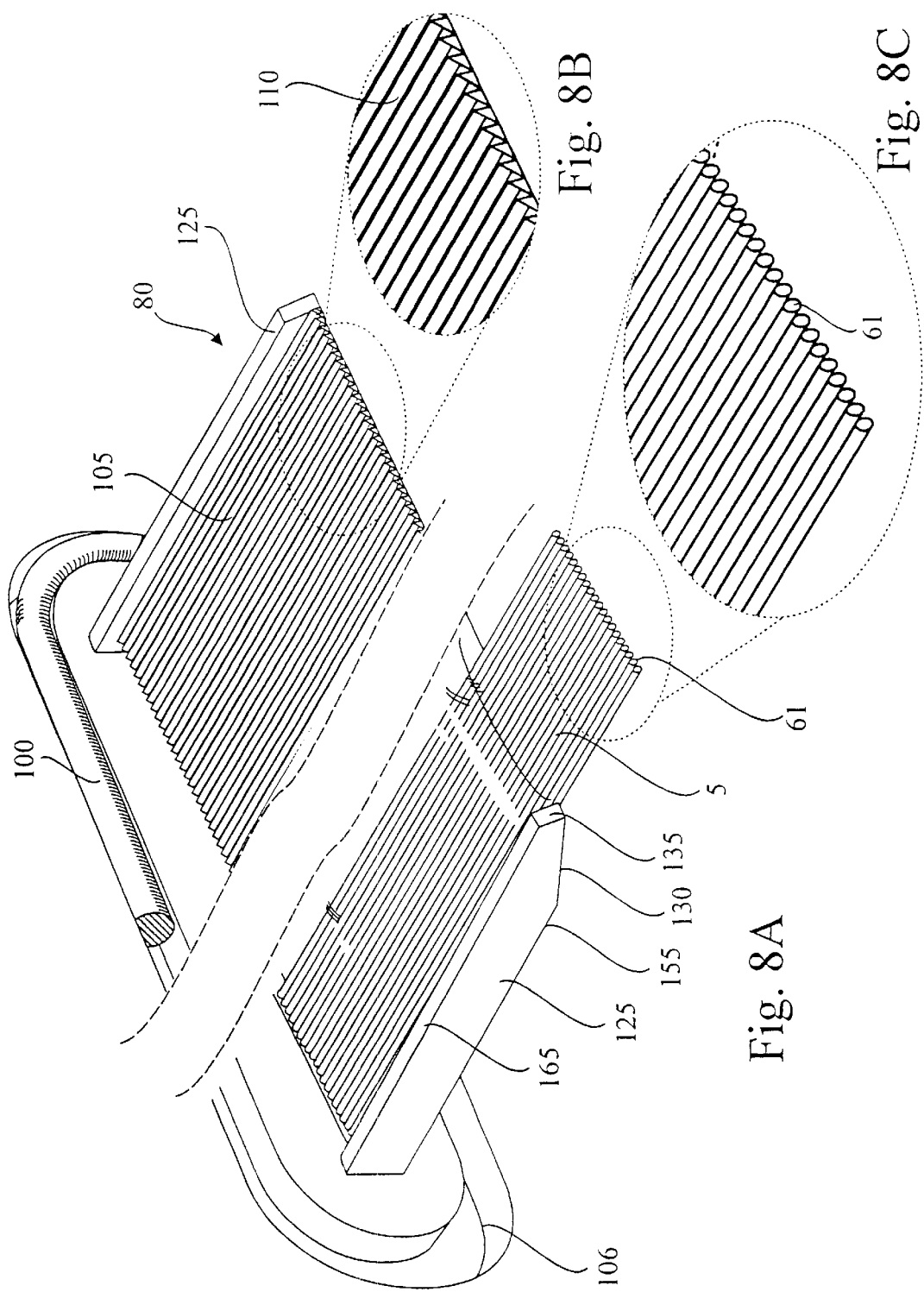
FIGS. 8a, 8b and 8c show an expanded perspective view of a platform portion of a preferred outlet support.
Figure 9:
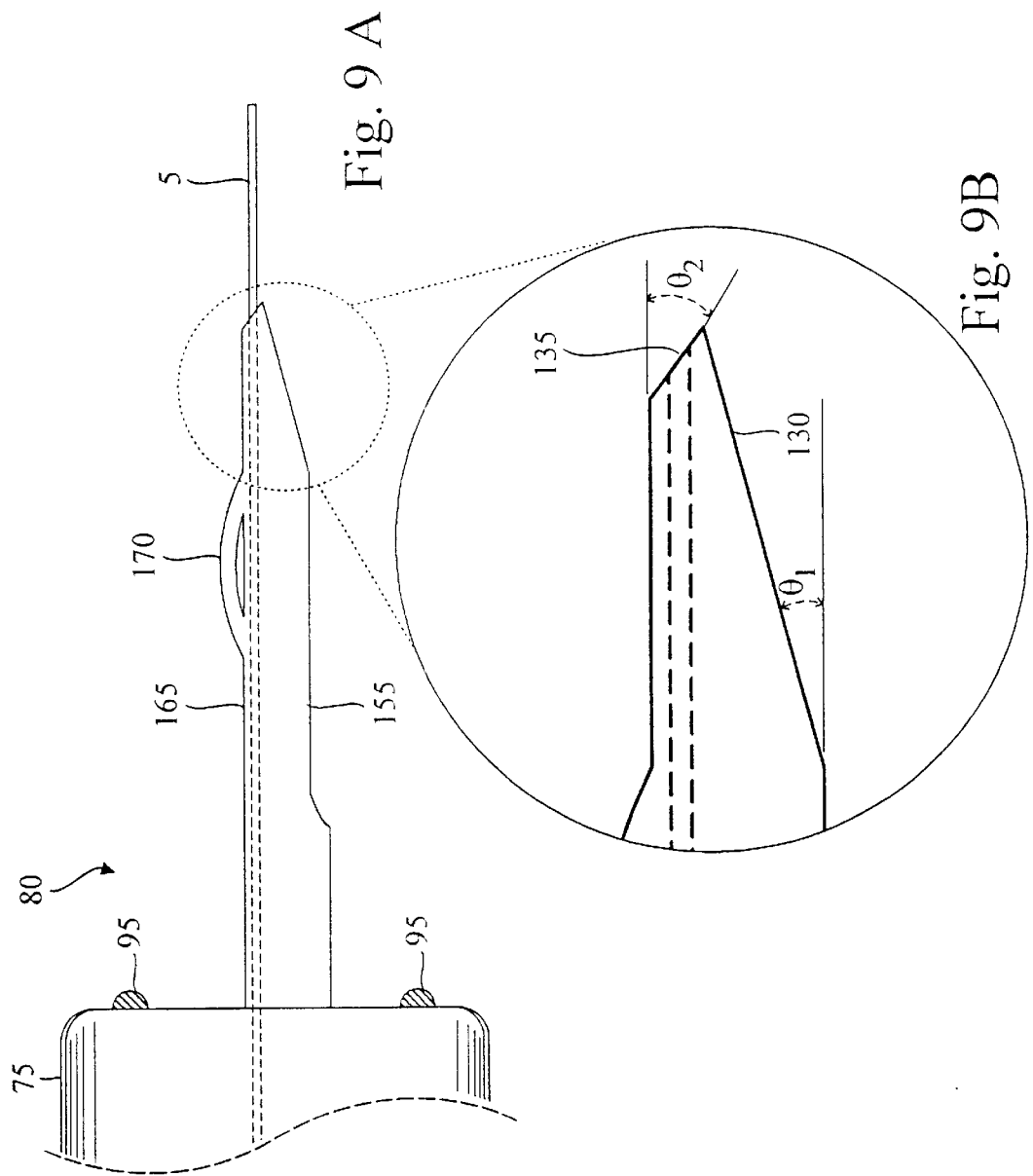
FIGS. 9a and 9b show a side view of a platform portion of a preferred outlet support.
Figure 10:
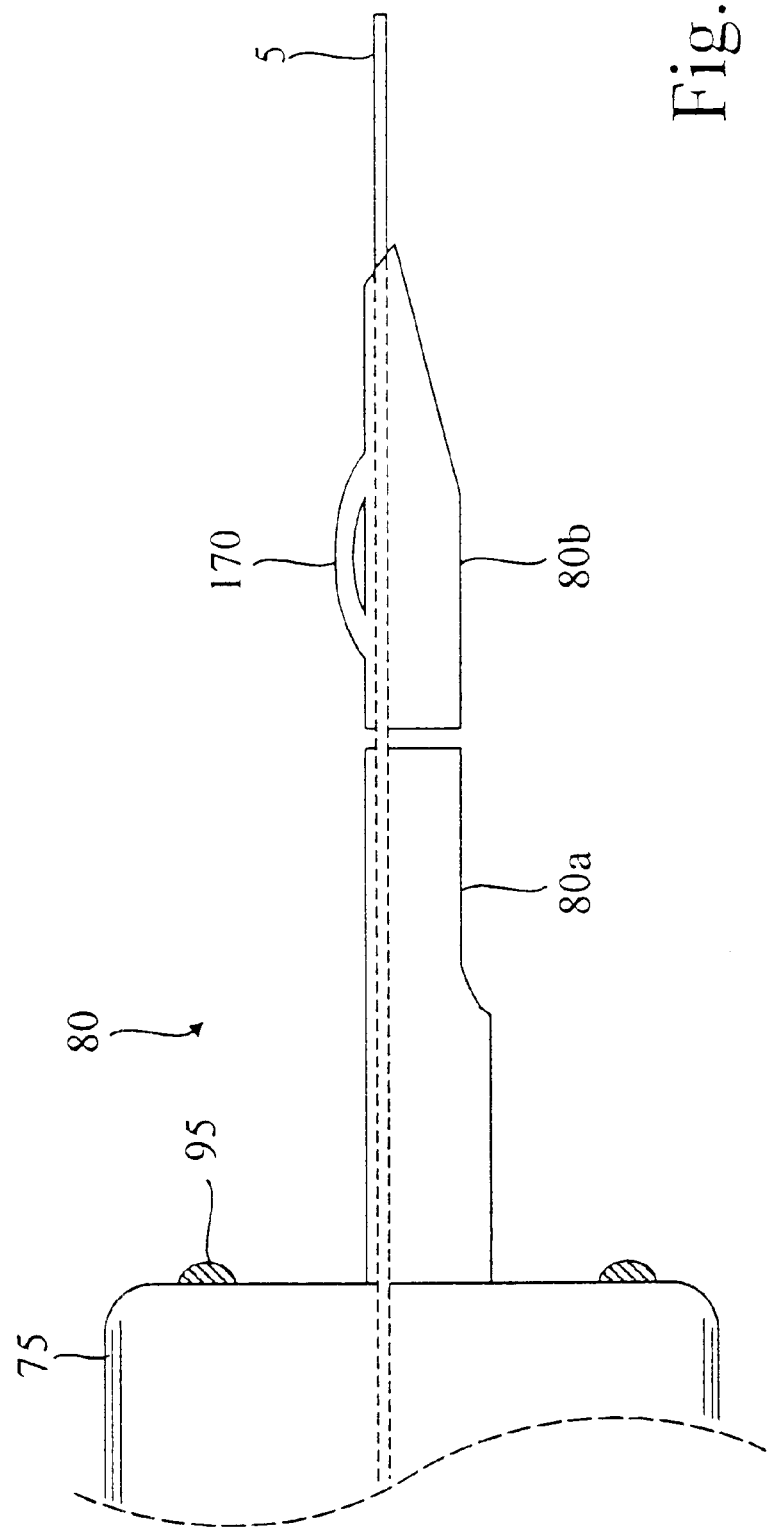
FIG. 10 shows a side view of an alternative platform portion of a preferred outlet support.

Details of the platform 80 of the preferred outlet support are shown in FIGS. 8–10. The platform 80 includes a support surface 105 including grooves 110 located thereon to precisely position capillary outlets 61 with respect to the platform and to each other. As was the case for the inlet support, the capillaries are preferably potted into the grooves of the outlet support with a potting material (not shown). Preferably, the platform holds the capillary outlets 61 in a linear array such that the capillary outlets are located on a line perpendicular to a longitudinal axis of the capillary outlets. This arrangement provides for simultaneous "side" illumination of a detection zone proximate to the capillary outlets using a single stationary light beam.

The platform 80 further includes guide rails 125 and chamfer features 130 and 135 that serve to effect smooth insertion of the platform into a receiving slot of a cuvette assembly. As most clearly shown in FIG. 19, the guide rails further serve to define an upper flow path 140 and a lower flow path 145 above and below the support surface 105 of the platform when the platform is inserted into a receiving slot 190 of the cuvette 150. Guide rails 125 include a bottom surface 155 for contact with an interior surface 160 of the cuvette. To ensure rigid positioning of the platform within the cuvette the contours of the bottom surface 155 should be such that the bottom surface is in intimate contact with the interior surface 160 of the cuvette over a substantial portion of the length of the guide rail.

While the figures show only two guide rails, one on each edge of the platform, more guide rails may be used, e.g., one or more central rails running along the top and/or bottom center portion of the platform parallel to the peripheral guide rails 125. In a preferred embodiment, the top or bottom central rails are made from a resilient material such that the rails cause the platform to be securely seated in the receiving slot. These additional rails may serve to inhibit bowing of the platform when in the receiving slot. Such bowing could be disadvantageous because it could cause a lack of uniformity of the flow of sheath fluid across the platform and loss of optical alignment of the capillary outlets, particularly as the width of the platform is increased.

As most clearly illustrated in FIGS. 9 and 10, a top surface 165 of the guide rail preferably includes one or more flexure features 170 for producing a compressive force between the interior surface 160 of the receiving slot of the cuvette and the platform thereby fixedly positioning the platform within the receiving slot. The flexure feature 170 of the preferred embodiment comprises a compressible protrusion located on the top surface 165 of the guide rail. This flexure feature may be formed by molding or machining the top surface of the guide rail.

To facilitate insertion of the platform 80 into the receiving slot 190 of the cuvette 150, the guide rails 125 may further include chamfer features 130 and 135. These chamfer features serve to guide the platform into the receiving slot such that there is a reduced likelihood that the capillary outlets will be mispositioned or broken during the insertion of the outlet support into the receiving slot. In a preferred embodiment depicted in FIGS. 9a and 9b, the chamfer feature consists of an upper chamfer surface 135 and a lower chamfer surface 130. An angle $\theta_1$ between the bottom surface 155 and the lower chamfer surface 130, and an angle $\theta_2$ between the top surface 165 and the upper chamfer surface 135 preferably ranges between about 10 and 80 degrees. More preferably, $\theta_1$ ranges between about 20 and 70 degrees, and $\theta_2$ ranges between about 20 and 70 degrees.

In an alternative embodiment of the platform portion of the outlet support shown in FIG. 10, the platform is divided into a first portion 80a and a second portion 80b, wherein the first and second portions are connected by the capillary tubes themselves. In this configuration, the capillary tubes act as a flexible hinge allowing second portion 80b to align itself in the receiving slot with reduced interference from the base 75 or the first portion 80a, thereby facilitating the positioning of the platform in the receiving slot.

II. Cuvette Assembly.

The cuvette assembly of the present invention provides a sheath-flow detection cell that operates in concert with the outlet support of the capillary array assembly to provide for easy removal and insertion of the capillary array. Specifically, the cuvette assembly provides (1) a detection zone within which to perform simultaneous optical measurements of material fluting from outlets of a plurality of capillary electrophoresis tubes with a minimum of light scattering or other optical nonidealities, (2) a sheath-flow cell including means for providing a sheath fluid, (3) means for introducing fluids into the capillary outlets under high pressure, e.g., to wash the interior of the capillary tubes and/or to introduce fresh electrophoretic separation media into the capillary tubes, and (4) means for removably mounting the capillary array assembly into the cuvette assembly.

Generally, a cuvette assembly in accordance with a preferred embodiment of the invention comprises (1) a cuvette to receive the outlet support of the capillary array and within which to perform optical measurements, (2) a clamping block for providing support for the cuvette, and (3) a plumbing block with associated fluidics for conducting fluids into and out of the cuvette.

1. The Cuvette.

Figure 11:
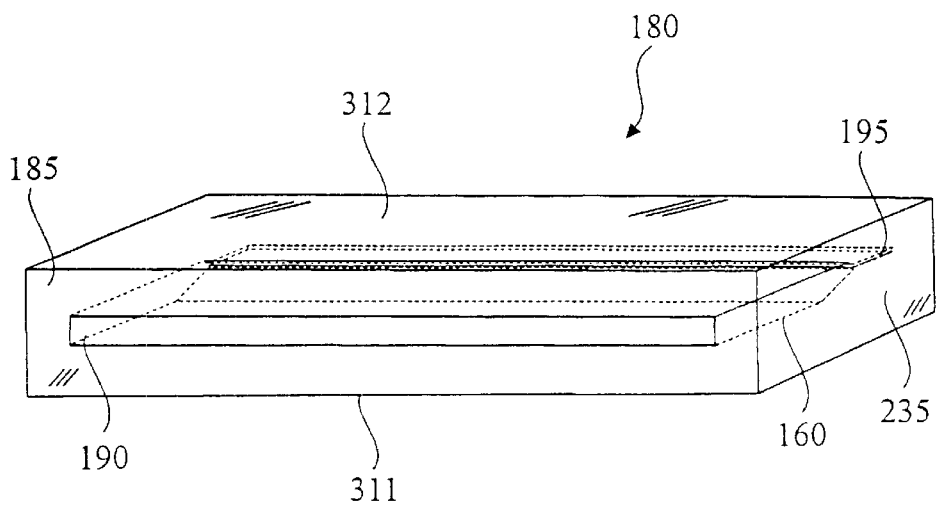
FIG. 11 shows a perspective view of a preferred cuvette with a receiving slot in the foreground.
Figure 12:
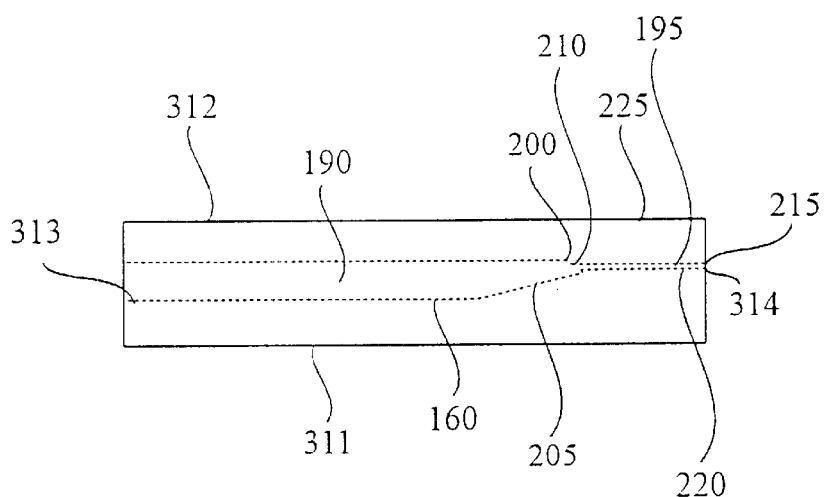
FIG. 12 shows a side view of a preferred cuvette.
Figure 13:
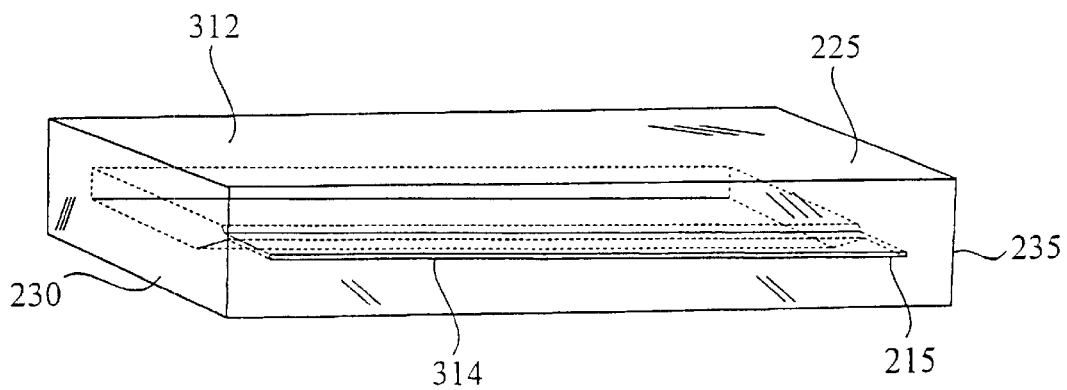
FIG. 13 shows a perspective view of a preferred cuvette with a gap region in the foreground.

A cuvette 180 of the preferred embodiment of the invention is shown in FIGS. 11–13. The cuvette 180 comprises a body 185, a receiving slot 190 for removably receiving the platform 80 of the outlet support 15 and for forming flow channel 140 and 145 in cooperation therewith, and a gap region 195 within which to perform an optical measurement.

In an important feature of the present invention, an interior surface 160 of the receiving slot 190 is adapted to conform with the guide rails 125 of the platform 80 such that when the platform is removably inserted into the receiving slot the platform is securely seated therein, where, as used herein, the term "removably inserted" or "removably received" means that the platform is received by the receiving slot of the cuvette in such a way that the platform may be removed by a user without disassembly of the cuvette or capillary array. In particular, the interior surface 160 of the receiving slot 190 includes a surface for contacting a bottom surface 155 of the guide rails, and a flexure-contact surface for contacting a top surface 165 of the guide rails, and for contacting the flexure-features 170 located on the of the top surface 165 of the guide rails. When the platform is securely seated in the receiving slot, upper 140 and lower 145 flow paths are formed.

The gap region 195 comprises a channel that is in fluid communication with the receiving slot 190. Thus, an inlet-end 210 of the gap region connects with the receiving slot and an outlet-end 215 of the gap region is distal to the receiving slot. Preferably, the gap region 195 has a vertical dimension that is smaller than that of the receiving slot, where, the vertical dimension is orthogonal to the plane of the array of capillary tubes. Preferably, the vertical dimension of the gap region is approximately equal to the outside diameter of the capillary tubes. Thus, typically the vertical dimension of the gap region 195 is between about 100 $\mu$m to about 1000 $\mu$m.

The gap region 195 further includes detection zone 220 in which samples emerging from the outlets of the capillary tubes are detected by a detector 227, e.g., a photomultiplier tube (PMT), charged coupled device (CCD), and the like, and, if fluorescent detection is used, where the samples are excited with a light beam. The detection zone is located adjacent to the capillary outlets. The location of the detection zone with respect to the capillary outlets should be far enough away from the capillary outlets so as to reduce light scattering caused by the capillary tubes, but, not so far away from the capillary outlets that samples emerging from the capillary tubes are excessively diluted and/or deformed by the sheath flow such that a band profile is substantially distorted thereby leading to a loss of resolution. Preferably, the detection zone 220 is located between about 20 $\mu$m and 2000 $\mu$m from the capillary outlets, and more preferably, between about 100 and 500 $\mu$m from the capillary outlets.

Figure 17:
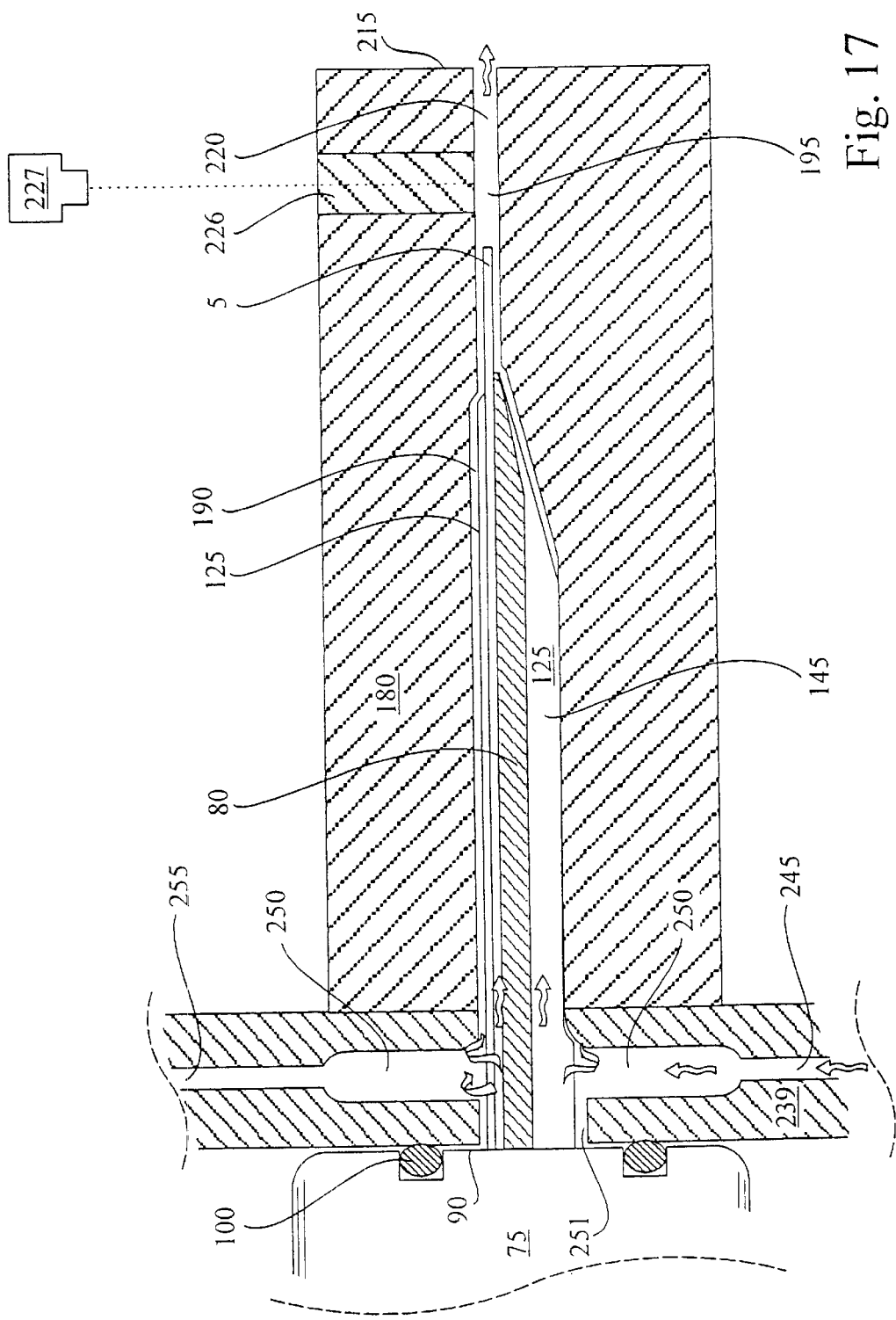
FIG. 17 shows a cross-section of a preferred operational combination of an outlet support, front plumbing block, and cuvette.

In an important feature of the gap region 195 of the cuvette, at least one of the walls of the cuvette 180 bounding the detection zone 220 of the gap region includes a window that is substantially transparent to light so as to provide optical communication between the detection zone and a detector located outside of the cuvette thereby facilitating detection of samples emerging from the capillary tubes into the gap region. For example, as shown in FIG. 17, a top wall 225 of the cuvette bounding the detection zone contains a window 226 that is transparent to light. Where fluorescence detection is used, it is also preferred that one or both side walls of the cuvette, 230 and/or 235, also include a window that is transparent to light to allow for an excitation radiation to enter the detection zone in the plane of the capillary outlets, e.g., a laser beam or other light beam, to effect fluorescence excitation of samples in the detection zone.

In a particularly preferred embodiment, the entire cuvette is formed from a rigid, chemically inert and optically transparent material, e.g., glass, quartz or fused silica.

2. Clamping Block.

In another significant aspect of the preferred embodiment of the present invention, exterior walls of the cuvette are supported by a clamping block. The purpose of the clamping block is to restrain exterior surfaces of the cuvette in order to prevent bowing and/or deflection of such surfaces due to high pressures within the cuvette. Such bowing and/or deflection is disadvantageous because it can lead to tensile stresses within the cuvette, e.g., at corners, that may cause mechanical failure of the cuvette.

In a preferred embodiment of the clamping block of the present invention, the clamping block comprises a first support for contacting a first external surface of the cuvette, a second support for contacting a second external surface of the cuvette, and a clamp for urging the first support and the second support against the first and second external surfaces of the cuvette.

Figure 14:
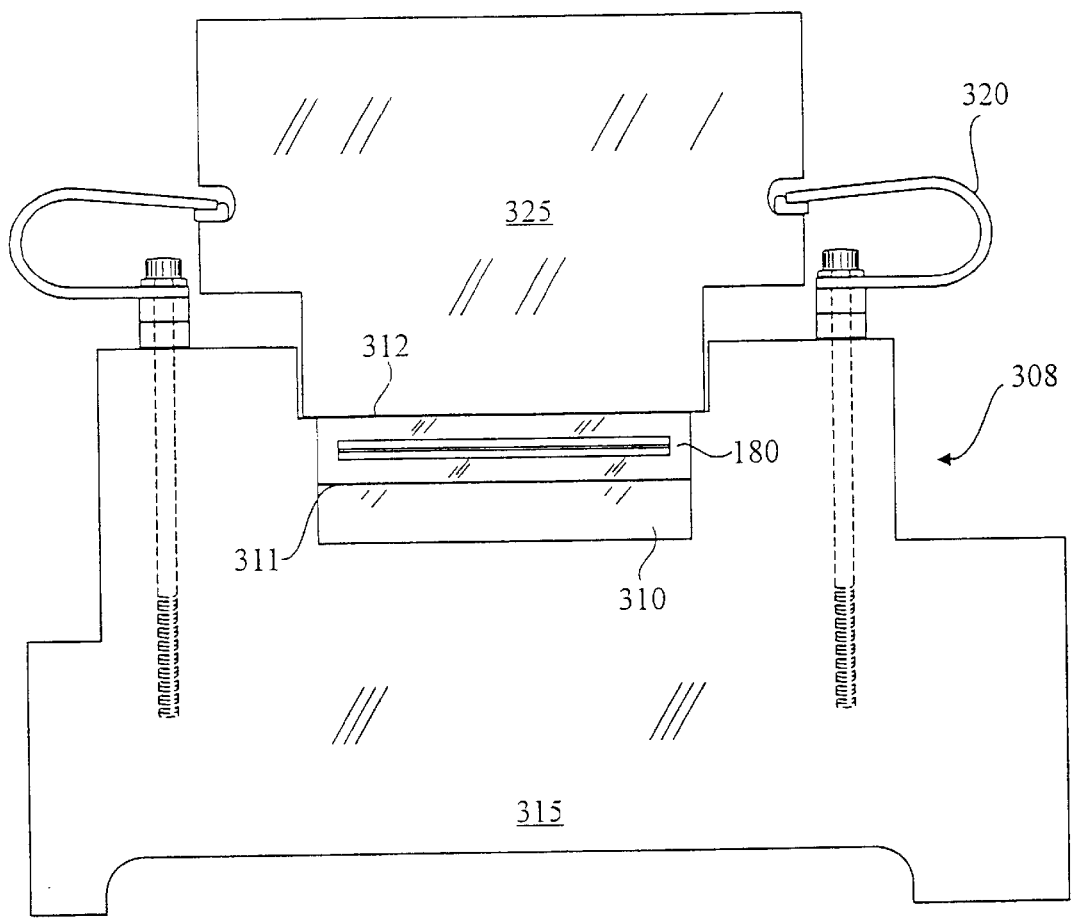
FIG. 14 shows a front view of a preferred cuvette located in a clamping block of the present invention.

A front view of a cuvette 180 located in a clamping block 308 is shown in FIG. 14. The clamping block depicted in FIG. 14 includes bottom support 310 for supporting a bottom surface 311 of the cuvette 180, a top support 325 for supporting a top surface 312 of the cuvette, and biasing means 320 for providing a compressive force for urging the top support, cuvette and bottom support together. Preferably, the top support 325 includes a window for providing optical communication between a surface of the cuvette and a detector and/or light source located proximate to the top support. For example, the top support may be made from optical quality glass, e.g., BK7 glass.

The compressive force supplied by the biasing means 320 should be greater than the lifting force generated by the internal operating pressure of the cuvette. In the preferred embodiment described here, typical compressive forces range from about 50 lbs. to about 400 lbs.

3. Plumbing Block and Associated Fluidics.

In another important aspect of the cuvette assembly of the preferred embodiment, the cuvette assembly includes a plumbing block (1) for controlling the flow of sheath fluids through the cuvette, and (2) for directing fluids into the outlets of the capillary tubes making up the capillary array, e g., solutions for washing the capillary tubes and/or fresh separation media. The plumbing block is located such that it is in fluid communication with the receiving slot 190 and the gap region 195 of the cuvette 180.

A preferred plumbing block according to the present invention is composed of a front plumbing block and a rear plumbing block wherein the front plumbing block abuts and is in fluid communication with an inlet 313 of the receiving slot of the cuvette, and the rear plumbing block abuts and is in fluid communication with an outlet 215 of the gap region of the cuvette.

Figure 15:
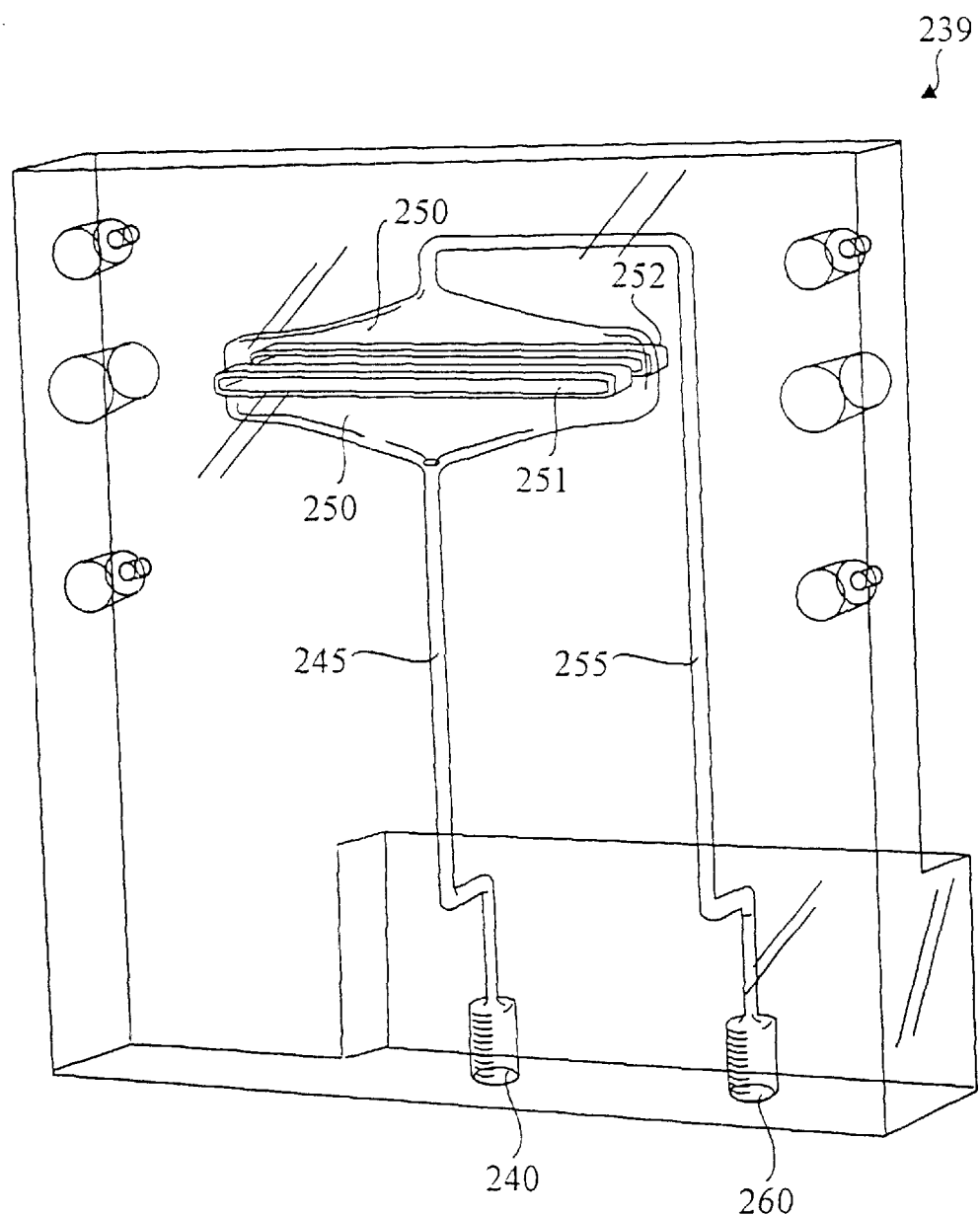
FIG. 15 shows a perspective view of a preferred front plumbing block.
Figure 16:
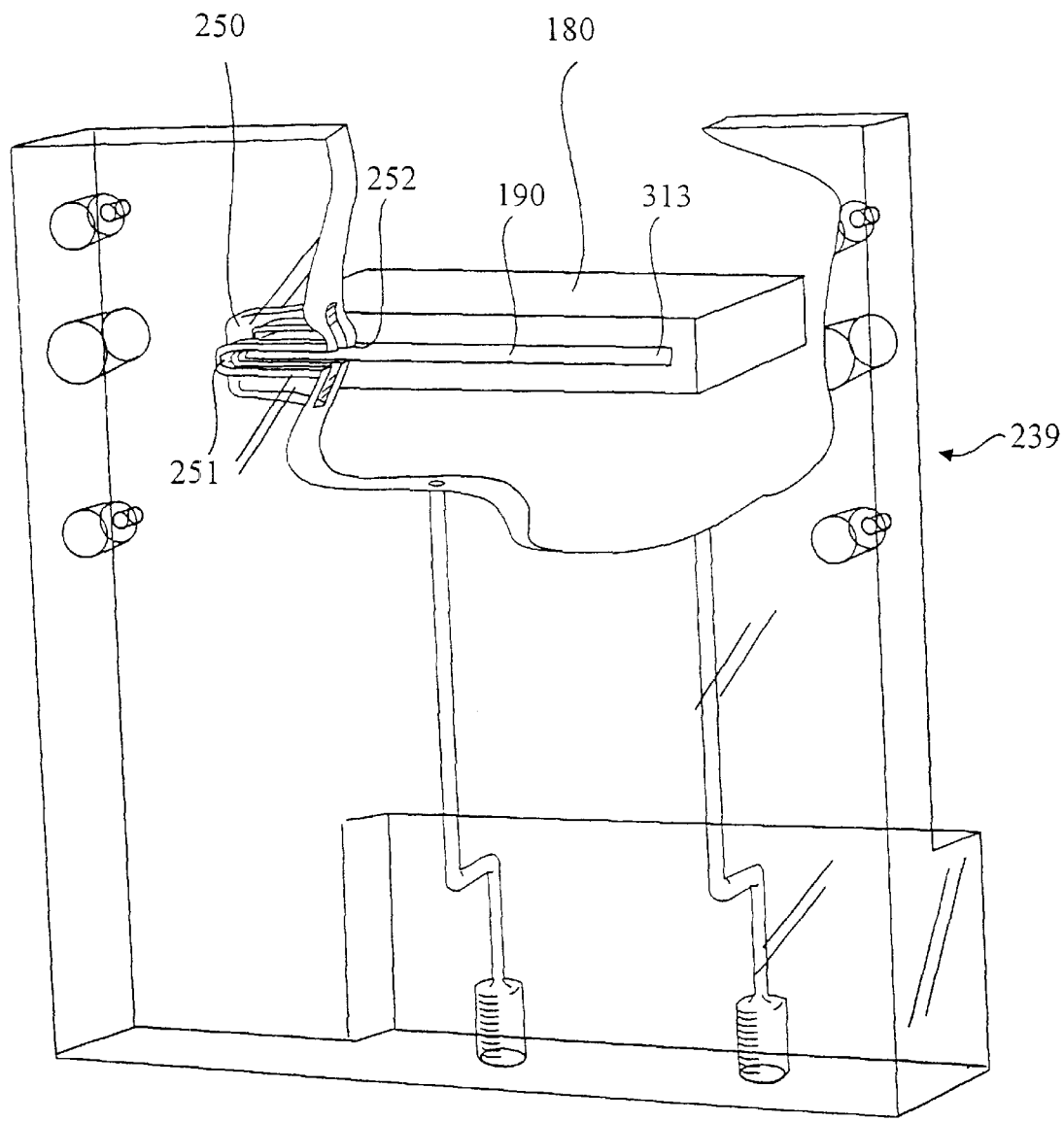
FIG. 16 shows a cutaway view of a preferred front plumbing block and a cuvette located behind the front plumbing block.

Various views of a front plumbing block 239 of a preferred embodiment of the invention are shown in FIGS. 15 and 16. Referring to FIG. 15, the front plumbing block 239 comprises an inlet port 240, an inlet channel 245, a front plenum 250, an outlet channel 255, and an outlet port 260. The front plenum includes an entrance slot 251 and an exit slot 252. The inlet port 240 and inlet channel 245 serve to conduct fluid into the front plenum 250 of the front plumbing block. An inlet valve (not shown) may be included to regulate the flow of fluid into and through the inlet channel 245. The outlet channel 255 and outlet port 260 serve to conduct fluid from the front plenum 250 and out of the front plumbing block to facilitate flushing fluid out of the cuvette and associated fluid passages. An outlet valve (not shown) may be included to regulate the flow of fluid into and through the outlet channel.

FIG. 16 shows the spatial relationship between the cuvette 180 and the front plumbing block 239. As indicated in the figure, the entrance 313 to the receiving slot 190 of the cuvette 180 abuts and is fluid communication with the exit slot 252 of the front plenum. Thus, fluid leaving the front plenum 250 through the exit slot 252 will enter the entrance 313 to the receiving slot 190 of the cuvette 180.

Figure 18:
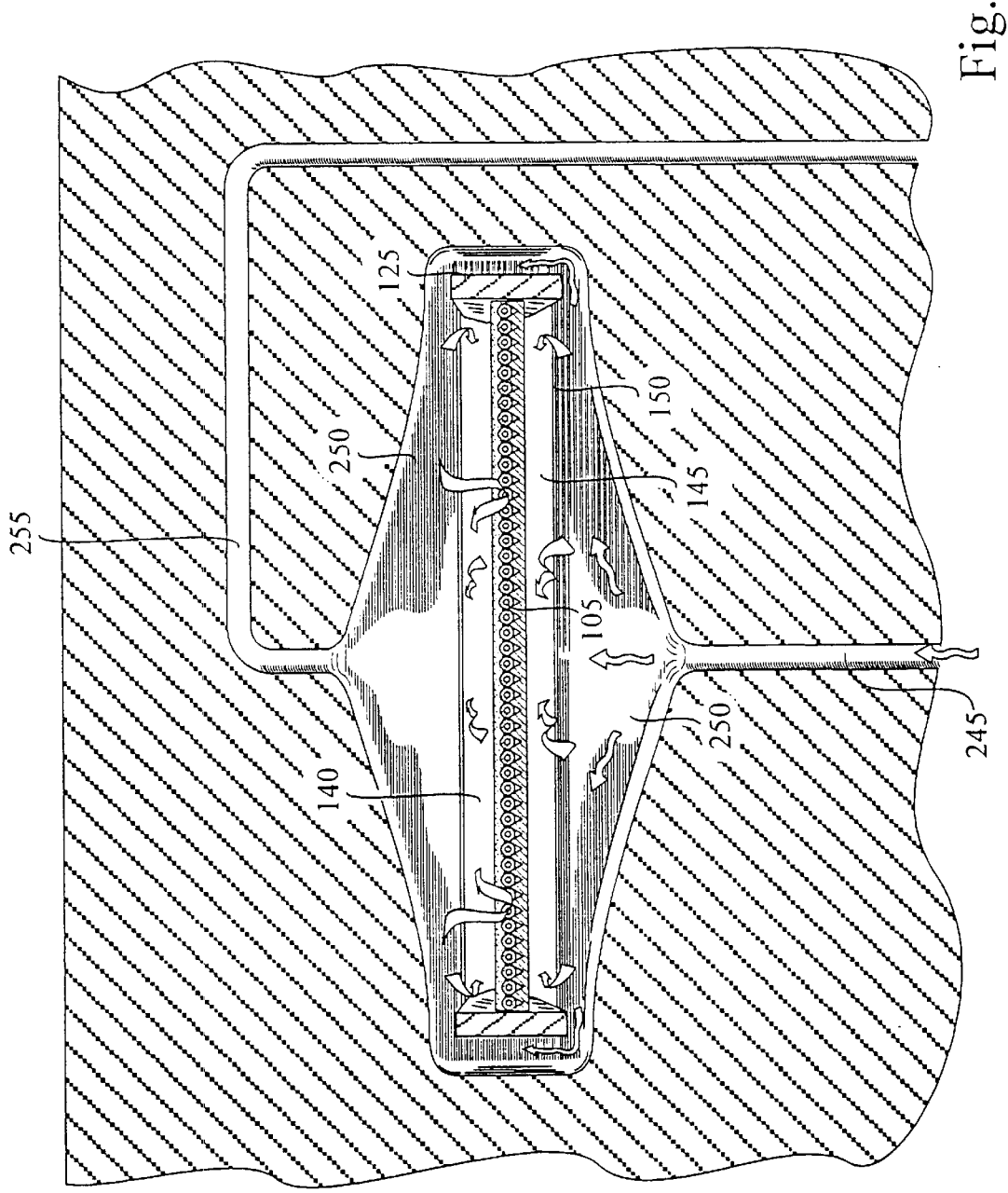
FIG. 18 shows a cross-section through the front plumbing block of FIG. 17.
Figure 19:
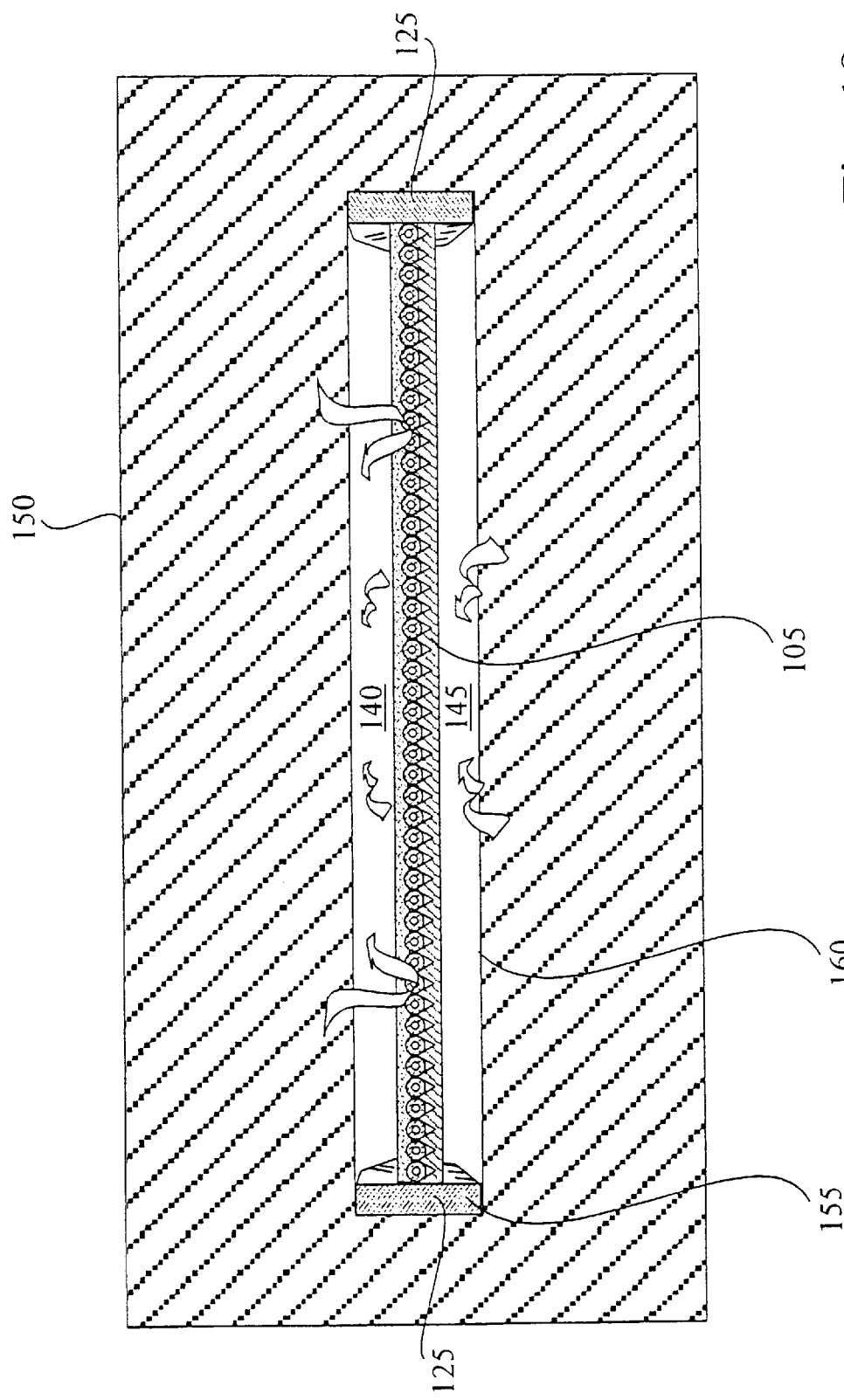
FIG. 19 shows a cross-section through the cuvette and platform portion of the outlet support of FIG. 17.

FIGS. 17–19 show various views of the spatial relationship among the platform 80 of the outlet support 15, the front plumbing block 239, and the cuvette 180 of a preferred embodiment of the invention when the platform is inserted through the front plumbing block and into the receiving slot of the cuvette.

Thus, as can be seen in the figures, fluid enters the front plumbing block 239 through the inlet channel 245 and into the front plenum 250 of the front plumbing block. Fluid is prevented from leaving the front plenum through the entrance slot 251 of the front plenum by the seal formed between the front face 95 of the base 75 of the outlet support and the front plumbing block 239. As most clearly shown in FIGS. 18 and 19, fluid then leaves the front plenum 250 through exit slot 252 of the front plenum and enters the receiving slot 190 through upper 140 and lower 145 flow channels formed between the guide rails 125, the interior surface of the receiving slot 190 and the support surface 105 of the platform 80. Fluid then flows out of the receiving slot into the gap region 195 of the cuvette, around the outlets 61 of the capillary tubes 5 and out of the gap region through the outlet end 215 of the gap region.

Figure 20:
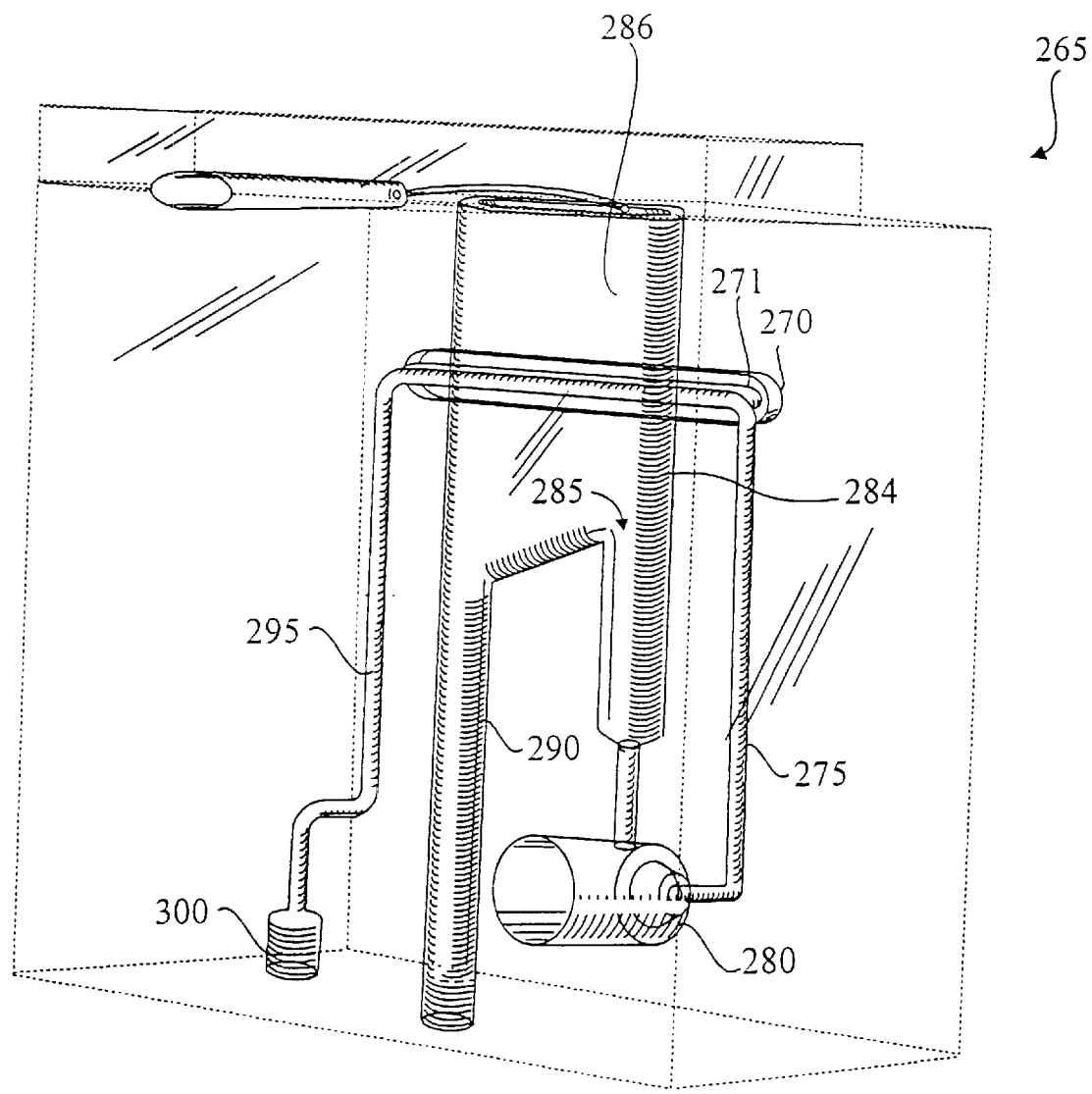
FIG. 20 shows a see-through view of a preferred rear plumbing block.

In a preferred embodiment, the plumbing block further includes a rear plumbing block abutting and in fluid communication with the outlet 215 of the gap region 195 of the cuvette 180. A see-through view of the rear plumbing block of a preferred embodiment is shown in FIG. 20. The rear plumbing block 265 includes rear plenum 270, rear plenum exit channel 275, waste valve port 280 with an associated waste valve (not shown), weir 285, weir head space 286, waste channel 290, fill channel 295, and fill port 300 with associated fill valve (not shown). The rear plenum includes an entrance slot 271 that is in fluid communication with the outlet 215 of the gap region 195 of the cuvette 180. The waste valve port generally includes a waste valve (not shown) located therein such that flow between the plenum exit channel 275 and the weir 285 may be controlled. The weir head space 286 is open to atmosphere to ensure atmospheric pressure in the weir. The rear plenum serves to conduct fluid leaving the gap region of the cuvette into the rear plumbing block such that the pressure at the capillary outlets is uniform across the capillary array, i.e., the pressure at each of the capillary tube outlets is substantially the same. The rear plenum exit channel 275 serves to conduct fluid out of the rear plenum 270 and into the waste valve port 280.

In an important feature of the present invention, the height of the weir 285 is adjusted so as to substantially eliminate any pressure drop between the inlet and outlet ends of the capillary tubes. This is important because any pressure drop across the capillaries may cause a pressure-driven flow having a parabolic flow profile that can lead to a substantial loss of electrophoretic resolution. Thus, the height of the weir is preferably set such that an hydraulic elevation at the top of the weir is approximately equal to an hydraulic elevation of the fluid in which the capillary inlets are submerged. In certain circumstances, it may be preferable to set the hydraulic elevation of the weir slightly less than the hydraulic elevation at the capillary inlet in order to take into account any pressure caused by the flow of the sheath fluid. As used herein, the term "hydraulic elevation" refers to a distance normal to the earth's surface above a reference elevation.

Fill channel 295 and fill port 300 serve to provide means for flowing a fluid into the rear plenum 270 of the rear plumbing block 265, and into the gap region 195 of the cuvette, and into the outlets of the capillary tubes. A fill valve (not shown) is positioned adjacent to the fill port to control flow therethrough. Typically, the fill port and fill channel are used to conduct fresh separation media and/or wash solutions into the outlets of the capillary tubes.

The fluid is driven into the fill port by a pumping system. Preferably, the pumping system is capable of high-pressure operation, i.e., above 200 psi, and is constructed such that materials used in parts of the pump that contact the fluid are formed from materials that are chemically inert to common fluids used in the system, e.g., water, acid, and organic solvents. Preferred materials include glass, and certain plastics, e.g., Teflon and Kel-F. In addition, preferably the pumping system includes a pressure sensor for monitoring the output pressure of the pump, and a multi-port distribution valve. Exemplary components of a preferred pumping system include a Cavro Model XL 3000 syringe pump, an Entran Model EPX-VO pressure sensor, and a Rheodyne RV Series motorized multi-position valve.

Preferably, the rear plumbing block 265 serves to house an electrode (not shown) that is positioned in an electrode reservoir 284 located between the waste valve port 280 and the weir 285. The electrode is in electrical communication with the capillary outlets 61. The electrode reservoir is preferably vented to atmosphere to eliminate any back-pressure caused by the build up of gases formed by electrolysis at the electrode during electrophoresis.

During electrophoresis, sheath fluid is conducted through the plumbing block and the cuvette assembly as follows. The inlet valve associated with the inlet port 240 is open, the outlet valve associated with outlet port 260 is closed, the fill valve associated with the fill port 300 is closed, and the waste valve associated with the waste valve port 280 is open. Thus, during electrophoresis, the sheath fluid is pumped into the front plumbing block through the inlet port 240, flows through the inlet channel 245, into the front plenum 250, out the front plenum exit slot 252, through the receiving slot 190 of the cuvette, across the support surface 105 of the platform 80, into the gap region 195 of the cuvette 180, past the capillary outlets 61, into the rear plenum 270, through the rear plenum exit channel 275, over the weir 285, and out the waste channel 290. Note that in a particularly preferred embodiment of the invention, in order to eliminate flow and/or electrical discontinuities in the system, the sheath fluid and the separation medium are the same material, e.g., a flowable non-crosslinked polymer solution.

When a fluid is being introduced into the capillary tubes through the capillary outlets, e.g., when the capillary tubes are being filled with fresh separation media or washed/regenerated with a wash solution, e.g., nitric acid or sodium hydroxide, the valves are positioned as follows. The inlet valve associated with the inlet port 240 is closed, the outlet valve associated with outlet port 260 is closed, the fill valve associated with the fill port 300 is open, and the waste valve associated with the waste valve port 280 is closed. Thus, fresh separation medium is directed into the fill port 300, through the fill channel 295, into the rear plenum 270, through the gap region 195 and into the capillary outlets 61, through the capillary tubes 5, and out the capillary inlets 60. Alternatively, when the cuvette is being flushed to exchange fluids, remove bubbles or simply wash the cuvette, each of the valves is positioned as above, with the exception that the outlet valve associated with outlet port 260 is open.

IV. Additional Features.

The electrophoresis device of the invention of course also includes other elements required to conduct a capillary electrophoresis process, e.g., electrodes in electrical communication with the capillary inlets, a power supply connected to the electrodes for creating an electrical field within the lumen of the capillaries, optionally a computer to control the functions of the device and for data collection and analysis, a detector for detecting samples in the cuvette, and a temperature control device for controlling the temperature of the capillary tubes and cuvette. Details of these and other common features of an operable capillary electrophoresis device may be found in any number of available publications, e.g., *Capillary Electrophoresis Theory and Practice*, Grossman and Colburn, eds., Academic Press (1992).

All publications and patent applications referred to are herein incorporated by reference to the same extent as if each individual publication or patent application was specifically and individually indicated to be incorporated by reference.

Although only a few embodiments have been described in detail above, those having ordinary skill in the analytical chemistry art will clearly understand that many modifications are possible in the preferred embodiment without departing from the teachings thereof. All such modifications are intended to be encompassed within the following claims.

We claim:

1. A capillary array assembly comprising:

a plurality of capillaries, each capillary having an inlet end and an outlet end;

an inlet support fixedly attached proximate the inlet ends of the capillaries, wherein the inlet support comprises a body, and a registration feature; and an outlet support fixedly attached proximate the outlet ends of the capillaries, wherein the outlet support comprises a platform having a support surface with capillary alignment grooves located thereon, and two or more guide rails;

wherein the capillary inlets are arranged in a multi-tier configuration, with said multi-tier configuration being defined at least in part by (i) an upper tier comprising a first linear array of capillary inlets and (ii) a lower tier comprising a second linear array of capillary inlets; wherein the first and second linear arrays are disposed parallel to one another, and the inlets of the upper tier are offset laterally relative to the inlets of the lower tier.

* * * * *